Figure 1:
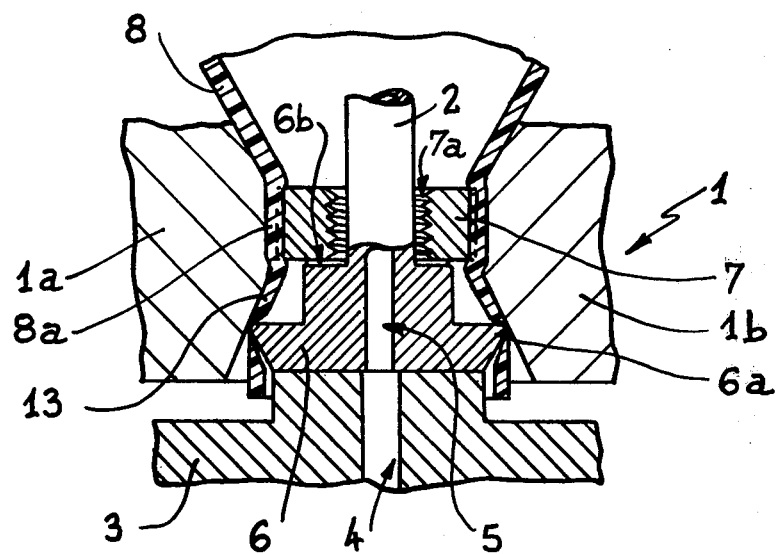

United States Patent [19]

Segalowicz

[11] 4,169,493

[45] Oct. 2, 1979

[54] FLEXIBLE HOT WATER BOTTLE

[76] Inventor: Joseph Segalowicz, 181 Ave. Renoir, 06210 Mandelieu, France

[21] Appl. No.: 904,415

[22] Filed: May 10, 1978

[30] Foreign Application Priority Data

May 13, 1977 [FR] France .................. 77 16031

[51] Int. Cl.² .................................. B65D 11/20
[52] U.S. Cl. ............................. 150/2.1; 150/8
[58] Field of Search .............. 150/2.1, 8; 264/98

[56] References Cited

U.S. PATENT DOCUMENTS

| 809,141 | 1/1906 | Schutz | 150/8 |
|---|---|---|---|
| 1,410,237 | 3/1922 | Baldwin | 150/8 |
| 1,442,358 | 1/1923 | Patterson | 150/2.1 UX |
| 1,488,886 | 4/1924 | Kraft | 150/8 |
| 1,607,963 | 11/1926 | Patterson | 150/2.1 |
| 1,994,127 | 3/1935 | Fenton | 150/2.1 |
| 3,705,931 | 12/1972 | Confer | 264/98 X |
| 3,919,374 | 11/1975 | Komendowski | 264/98 X |

Primary Examiner—Donald F. Norton
Attorney, Agent, or Firm—Fleit & Jacobson

[57] ABSTRACT

A hot water bottle having an internally threaded neck. The threaded neck is formed as an insert and the bottle is formed by blow moulding around the insert. The insert is preferably of material which will melt superficially during moulding to become welded to the actual neck of the bottle.

2 Claims, 6 Drawing Figures

FLEXIBLE HOT WATER BOTTLE

The present invention relates to an improved process for the moulding of hollow bodies, as well as to devices and moulds intended for the carrying out of this process.

The invention is more particularly concerned with the moulding of hollow bodies including an internally threaded neck and especially with flexible hot water bottles.

Articles of this kind are presently produced either from rubber or from thermo-plastic material. In the latter case, the part constituting the neck is overmoulded by injection on to a nut intended to form the internal part thereof. The known processes are complex and for this reason the sale price of the article thus obtained is relatively high. They require, moreover, very specialized personnel. These known processes consist principally in providing grooves in the periphery of the insert in such a manner that it is rigidly anchored angularly and longitudinally with respect to the neck of the bottle. It will be easily understood that such an anchorage cannot ensure sealing between the actual wall of the neck and the periphery of the insert.

The improvements which are the object of the present invention aim at remedying these disadvantages by providing a hollow body such as a hot-water bottle in a single blowing operation and in ensuring perfect sealing between the insert and the neck of the bottle.

To this effect, the insert is made from a material which is capable of being superficially melted when it is palced in contact with the parison intended for the blow-moulding of the hot water bottle body, so that it will be associated by a sealing weld with the corresponding wall of the neck of this bottle.

According to another feature of the invention, the parison intended to permit blowing of the body of the hot water bottle presents a perimeter greater than that of the mould cavity such that the periphery of the latter is pinched between the two halves of the split mould before the blowing operation.

The attached drawing, given by way of example, will facilitate a better understanding of the invention, the features thereof and the advantages which it is possible to gain.

Figure 2:
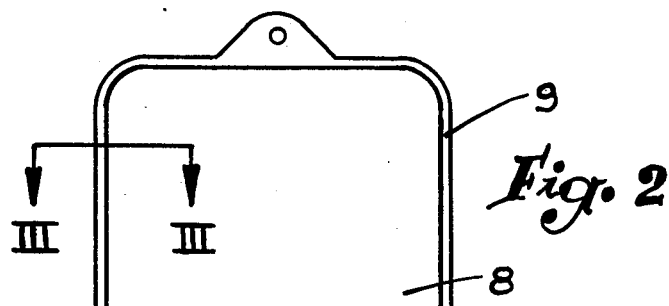
Figure 3:
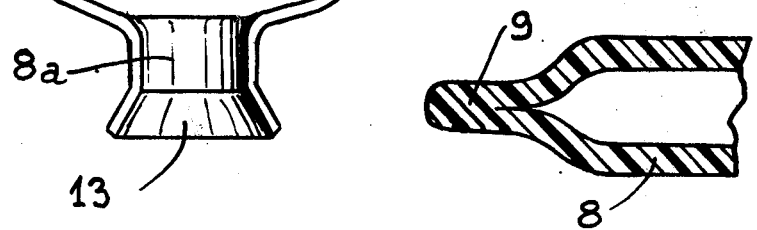
Figure 4:
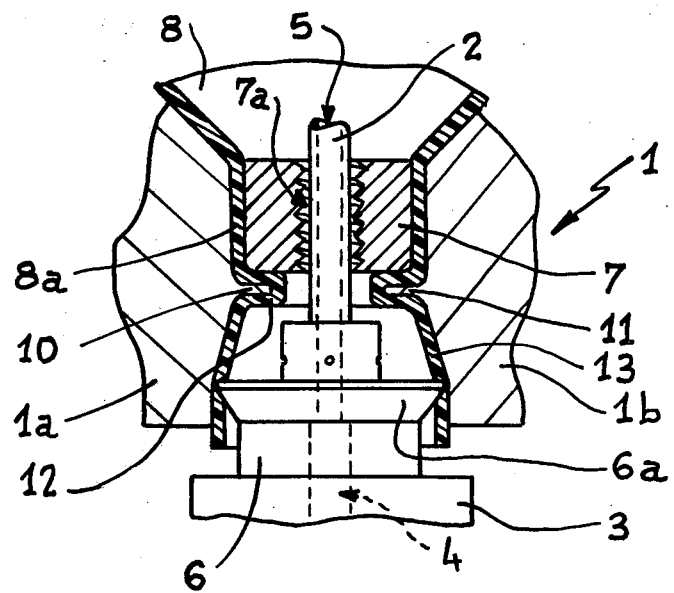
Figure 5:
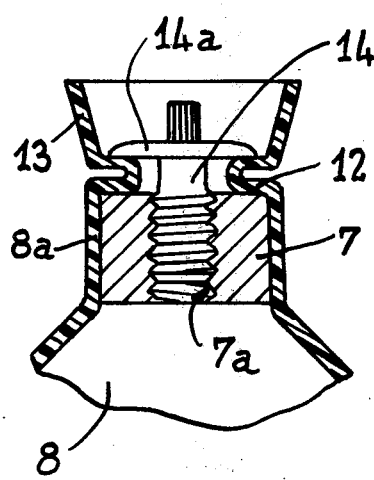
Figure 6:
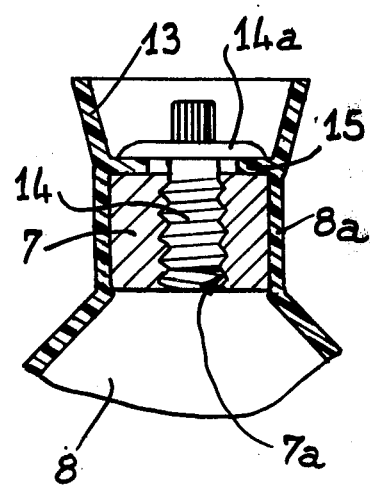

FIG. 1 is a sectional fragmentary view of a mould intended to permit the carrying out of the process of the invention, FIG. 2 is a view in elevation to a smaller scale of a hot water bottle of the invention, FIG. 3 is a section to a large scale along the line III—III (FIG. 2), FIG. 4 is a view similar to that of FIG. 1, but showing a modification adapted to enable a sealing joint to be made which is fast with the body of the hot water bottle, FIG. 5 is a partial view of a hot water bottle provided with its closure plug, and FIG. 6 is a view similar to FIG. 5, but showing another sealing joint fast with the neck.

There is shown very schematically and in fragmentary manner in FIG. 1, a split mould 1 for the blowing of a hollow body from the usual parison on to which close the two valves 1a, 1b of the split mould. This latter is mounted on a conventional machine including a blowing iron 2 rigid with a support 3. This support is provided with a hole 4 connected to a source of air under pressure, not shown, and which communicates with the bore 5 of the blowing iron 2. The latter includes a base 6 assembled on the support 3 and which includes a flange 6a of which the sharp peripheral edge constitutes a circular knife.

The base 6 constitutes an annular support for an insert 7 made in the form of a nut having a smooth circular periphery and which includes a threaded bore 7a. Grooves 6b are provided radially on the upper face of the base in such a manner that there is communication between the two spaces of the mould situated to either side of the insert 7. In known manner, this latter can be retained by any means with respect to the blowing iron 2 so as to immobilise it angularly and longitudinally.

Briefly, it will be recalled that in order to carry out blow moulding around a hollow blowing iron, a tubular mass or so called ball or parison is made which descends by gravity in heated state from the head of an extruder in order to surround the blowing iron and become disposed between the two halves 1a, 1b of the split mould which, of course, are connected by means for displacing them transversely with respect to the blowing iron.

According to the invention, a parison is made of which the perimeter is greater than that of the largest portion of the mould cavity so that the mould halves close on to the parison following the whole periphery of the cavity. Thus the periphery of the hot water bottle 8 (FIG. 2) is pinched before blowing between the two mould halves 1a, 1b in order to constitute a peripheral bead 9 which ensures before blowing a perfect welding of the periphery of the hot water bottle. After blowing and as shown in FIG. 3, there is the certainty of a perfect weld of the two faces of the bottle 8 at the level of its peripheral bead 9. This is all the more true if there is used for making the hot water bottle a material such as a thermoplastic elastomer which, in line with any solution for continuity of a cavity of a blowing mould, such as the plane of the joint of the two halves of this split mould, has a tendency to flow, constituting zones of less resistance which risk rupture during use.

As shown in FIG. 4, each of the mould halves 1a, 1b can include a blade part 10, 11 adapted to extend into the parison with a view to constituting a double-lipped joint 12 on the exterior of the insert 7. Of course, in this case, the insert should be held a certain distance above the base 6 of the support 3 as is well known in the art, so that the blade parts 10,11 can close without the insert being pushed upwardly along the blowing iron 2.

It will be easily understood that the air fed from the hole of the support 3 into the bore 5 of the blowing iron 2 passes across the space located between the periphery of the blowing iron 2 and the threaded hole 7a of the insert to permit the formation of a throat 13 beyond the insert 7 in a direction towards the exterior. It is of course the cutting edge of the flange 6a which, in known manner, cuts the end of this throat when the mould is closed.

It will be noted that in the case where the double-lipped joint is formed fast with the body of the hot waterbottle, the parison is not gripped at the level of the neck, this latter being cut in the manner in itself known by knives carried by each of the mould halves. Moreover, pinching of the wall member can be dispensed with in the case of moulding according to FIG. 1.

By virtue of the presence of the joint 12 the head 14a of a threaded plug (FIG. 5) screwed into the threaded hole 7a of the insert 7 will come to bear against the upper lip of said joint to compress it against the insert with a view to ensuring a perfect sealing at this level.

The choice is made to form the insert 7 in a thermoplastic material such that its smooth periphery can weld itself by superficial fusion to the internal face of the neck 8a of the hot water bottle. It is possible to heat the insert prior to placing it in position in the mould in order to facilitate the aforesaid fusion.

As shown in FIG. 6, it would be possible to form the hot water bottle by injection blowing, its neck being injected with a flat joint 15 at the same time as a preform which would then be shaped by blowing which is well understood in the art.

It should moreover be understood that the preceding description has been given only by way of example and that it in no way limits the field of the invention which will not be exceeded by replacing the described details of execution by any other equivalents.

I claim:

1. A flexible hot water bottle having the shape of a flat sack comprising:

an internally threaded neck portion formed by an insert of plastics material having a periphery subjected to superficial fusion; and a sack portion having a first portion fused to and extending above the periphery of said insert and a second portion integral with and extending below the periphery of said insert to form a sack, the sack having an external peripheral bead extending there around, the peripheral bead being formed by pinching together walls of a parison used to form the sack.

2. A flexible hot water bottle according to claim 1 further comprising a threaded plug member engageable with the internally threaded neck portion to seal the bottle, the plug member including a threaded portion insertable into the neck portion and a flange portion positioned above the threaded portion, the flange portion being adapted to contact and compress against said insert a part of said first portion of the sack portion extending above the periphery of said insert.

* * * * *